United States Patent [19]
Reis et al.

[11] Patent Number: 5,252,998
[45] Date of Patent: Oct. 12, 1993

[54] CONTACT EYEGLASS

[75] Inventors: Werner Reis; Andreas Plesch, both of München; Karl-Heinz Wilms, Emmering, all of Fed. Rep. of Germany

[73] Assignee: G. Rodenstock Instruments GmbH, Riemerling

[21] Appl. No.: 654,636
[22] PCT Filed: Jun. 19, 1990
[86] PCT No.: PCT/DE90/00461
  § 371 Date: Feb. 19, 1991
  § 102(e) Date: Feb. 19, 1991
[87] PCT Pub. No.: WO90/15570
  PCT Pub. Date: Dec. 27, 1990

[30] Foreign Application Priority Data
Jun. 19, 1989 [DE] Fed. Rep. of Germany ....... 3919985

[51] Int. Cl.$^5$ ............................................. G02C 7/04
[52] U.S. Cl. ................................. 351/160 R; 351/205; 351/206; 351/219
[58] Field of Search ............ 351/205, 206, 219, 160 R

[56] References Cited

U.S. PATENT DOCUMENTS

| | | | |
|---|---|---|---|
| 4,134,647 | 1/1979 | Ramos-Caldera | 351/219 |
| 4,410,245 | 10/1983 | Koester | 351/219 |
| 4,728,183 | 3/1988 | Heacock et al. | 351/219 |
| 5,046,836 | 9/1991 | Volk | 351/219 |

Primary Examiner—Bruce Y. Arnold
Assistant Examiner—Hung X. Dang
Attorney, Agent, or Firm—Antonelli, Terry, Stout & Kraus

[57] ABSTRACT

An instrument for the examination and/or treatment of the eye having an examination device designed for the examination of the fundus oculi and having a contact eyeglass, which is provided with a lens which can be placed on the eye, the eye-facing surface of the lens being adapted to the curve of the cornea. The lens which is placed on the eye has no spherical power at least in the region of the optical axis.

20 Claims, 2 Drawing Sheets

CONTACT EYEGLASS

TECHNICAL FIELD

The present invention relates to an instrument for the examination or the treatment of the eye with an examination device designed for examining the fundus oculi and with a contact eyeglass having a lens, which is to be placed on the eye and the surface of which that faces the eye is adapted to the curve of the cornea.

STATE OF THE ART

An instrument of this kind is known from the U.S. Pat. No. 4,213,678. In this prior art instrument, the optical power of the contact eyeglass, which is provided with two spherical surfaces, is taken into consideration in the calculation of the path of the beam of the actual examination device, which in this case is a scanning laser ophthalmoscope, so that the contact eyeglass is an indispensable part of the beam path.

However, there are a number of examination and treatment situations, in which the use of a contact eyeglass is troublesome:

One source, by way of illustration, is that the examining person has to hold the contact eyeglass with one hand thereby restricting him/her in handling the examination device and/or in performing other manipulations.

Furthermore, there are certain examination and/or treatment situations, in which an as large as possible "free space", i.e. an as large as possible distance between the apex of the eye and the apex of the final surface of the eye examination device, i.e. of the surface lying closest to the eye, is required.

For this reason, instruments for the examination and treatment of the eye have increasingly been proposed whose beam path is designed in such a manner that use of a contact eyeglass is obviated. Only by way of example, reference is made to the U.S. Pat. Nos. 4,764,005, 4,768,873 and 4,854,692 as well as EP-A 0145 563 in which scanning laser ophthalmoscopes are described which do not use a contact eyeglass.

Moreover, contact eyeglasses are known from DE-A-37 18 599 or the U.S. Pat. Nos. 4,560,962, 4,598,984, 4,664,490 or 4,728,183. These contact eyeglasses, however, are intended for the examination and/or treatment of the fundus oculi with an examination device, the optical design of which "actually" only permits the examination of the anterior portions of the eye. Examination devices of this type are, by way of illustration, slit lamp devices built in accordance with the optical design of the so-called slit lamp microscope for the examination of the cornea and the anterior portions of the eye. The use of these contact eyeglasses permits extending the area of application of such instruments even to the examination and/or treatment of the fundus oculi. The contact eyeglasses known from the aforementioned publications can, however, not be utilized in connection with eye examination devices designed to examine and/or treat the fundus oculi as "adding" the power of this examination device to the power of the contact eyeglass would yield an optical power that would make sharp focussing on the fundus oculi impossible.

It has turned out that ophthalmogists prefer slit lamps with additional contact eyeglasses as the instrument of examination, respectively of observation in laser treatment of the fundus oculi to devices, which are actually intended for the examination of the fundus oculi and with which no additional contact eyeglass is employed.

In accordance with the present invention it was understood that the reason therefor is probably that there are a number of problems involved in treating the fundus oculi without using a contact eyeglass:

By way of illustration, problems due to blinking, inevitable eye agitation and drying of the cornea from holding the eye open for longer periods without blinking as, by way of illustration, is the case when the eye is held open by a clamp. The drying of the cornea makes it deform and the image worsens substantially thereby.

DESCRIPTION OF THE INVENTION

The object of the present invention is to solve the problems arising from blinking, eye agitation, etc, especially, in laser treatment of the fundus oculi with an instrument designed for the examination of the fundus oculi.

An element of the present invention is that it was understood that the problems arising from blinking, eye agitation or holding the eye open with a clamp of an instrument designed for the examination of the fundus oculi can be solved also by utilizing a contact eyeglass in such a device. In accordance with the present invention, this contact eyeglass is however designed in such manner that in comparison to the prior art contact eyeglasses the lens placed on the eye has (practically) no spherical power in the region of the optical axis. In particular, this is understood to mean that in the region of the optical axis of the lens placed on the eye the spherical power D is:

$$-0.5 \text{ dpt} < D < 0.5 \text{ dpt}$$

In this case—if little spherical power is to be provided at all—it is preferably negative in order to compensate for the typical imaging errors of the examination instrument.

Due to the contact eyeglass without spherical power employed in accordance with the present invention, the beam path of the eye examination device, thus, by way of illustration, of the scanning laser opthalmoscope, does not change. Nonetheless it is ensured that blinking does not occur, which would be encumber the examination and/or laser treatment of the fundus oculi, and that the cornea does not become dry from holding the eyelid open as there is fluid between the surface of the lens facing the eye and the eye. Moreover eye agitation is reduced substantially due the contact eyeglass placed on the eye.

On the other hand, however, the eye examination device may continue to be employed without the contact eyeglass so that the physician may select using the examination device with or without the contact eyeglass depending on the examination and/or treatment situation.

Any examination instrument permitting an examination of the fundus oculi without an additional contact eyeglass can be utilized as an eye examination device in connection with the "zero contact eyeglass". Examination devices of this kind are, by way of illustration, conventional fundus cameras, ophthalmoscopes or so-called scanning laser opthalmoscopes as, by way of illustration, known from the EP-A-0 145 563, the Japanese patent publications 61-5730 and 50-138822, the German Patent 32 45 939 or the WO 88/ 03396. For this reason the construction of the examination device shall not be discussed in more detail herein.

As an element of the present invention it was understood that a normal human eye has monochromatic deviations for extra-axial beams, which worsen the imaging, especially in the peripheral regions of the eye. Therefore, it is particularly preferable if the lens placed on the eye has practically no spherical power in the region of the optical axis but is provided beyond the optical axis with additional "aspherical" power, which partially compensates for the monochromatic aberrations of the human eye. In accordance with a feature of the present invention, the aspherical surface is preferably the surface facing away from the eye, thus the surface, which is not placed on the eye, as there is a greater degree of freedom regarding "asphericity" in this surface than in the surface facing the eye, the contour of which essentially has to follow the curvature of the cornea.

As it was understood as an element of the present invention that the so-called Gullstrand model of the eye does not adequately describe the human eye, it is preferable if, in the approximation of the surface section by an ellipse the aspherical surface has a conic section coefficient K, with K being:

$$-0.85 < K < -0.7$$

It is expressly pointed out that the aspherical surface usually has no surface section, which is exactly elliptical in shape, but rather the surface section may deviate from the elliptical shape.

Generally, the aspherical surface is, furthermore, a rotational-symmetrical surface. In special cases, however, the aspherical deviations are not rotational-symmetrical. Moreover in the case of astigmatic eyes, a toric or an atoric surface may also be utilized, i.e. a surface with cylindrical power and not spherical main sections.

According to another feature of the present invention, at least one mirror is provided, which permits examination and/or treatment of the peripheral portions of the eye. By employing such an as such known mirror, the range of application is substantially extended, in particular, of a scanning ophthalmoscope used as the instrument of examination, which has a relatively small vertical, respectively horizontal, image angle of usually 30°. This mirror is preferably arranged outside the examination and/or treatment beam path for the center region and the examination of the center region therefore is not encumbered, permits an enlargement of the "horizontal image angle", but also with a corresponding turn of the contact eyeglass an enlargement of the "vertical image angle" particularly in a scanning laser ophthalmoscope, which usually has only one possible mode of rotation about a vertical axis, i.e. a possible adjustment in an almost horizontal plane.

Moreover, the deflection mirror can be designed in such a moveable manner that the fundus section to be examined can be continuously varied.

Naturally, it is possible to provide not only one deflection mirror, but also a number of deflection mirrors, which are brought consecutively into the beam path of the device by a corresponding rotation movement of the examination, respectively treatment, device and/or a corresponding turning of the contact eyeglass. The various sets of mirrors then permit the examination and/or treatment of different peripheral regions. It is especially preferable to provide two sets of mirrors, which are, in particular, tilted 90° toward each other and which permit examination and/or treatment of different peripheral regions.

In any event, however, it is advantageous if, the central examination and treatment region and the region, respectively regions, which can be examined via the mirrors, adjoin without overlapping. By way of illustration, in the case of a scanning ophthalmoscope with image processing connected thereafter the individual regions examined in a different manner can subsequently be represented on a monitor "seamlessly" one after the other.

The various mirrors may, naturally, be plane mirrors and/or prisms and therefore elements, which only deflect the beam path. However, it is just as possible that at least part of the mirrors have an optical power, which preferably can serve to at least partially compensate for the aberrations in the peripheral regions (claim 10) or that examination of the chamber angle becomes possible.

In the further improvements the lenses which can be placed on the eye and, if need be, the mirror or mirrors can be kept in an (as such known) contact eyeglass mounting, which is terminated on the side turned from the eye by a (clear, transparent) dust protection plate, respectively, cover plate. This dust protection plate may in accordance with the present invention assume additional functions:

Such a cover plate serves not only as dust protection, but also permits sterilizing the invented contact eyeglass, by way of illustration, "in solution". Above all, the cover plate can also assume optical functions:

In order to change the beaming-in angle, the cover plate may, by way of illustration, be designed conically.

Furthermore, reflexes can be minimized with an oblique cover plate. The cover plate and the mirrors may also carry markings (e.g. notches) in order to find the mirror setting more easily, so-called TABO markings etc.

Furthermore, additional elements such as wedge elements, lenses, etc. may be provided on the cover plate. In this case, it is preferable if the cover plate is exchangeable so that the various cover glasses, respectively cover plates, can be inserted consecutively The invented contact eyeglass does not only extend the (horizontal and vertical) image angle of available eye examination instruments for the fundus oculi, but in addition also permits examination and/or treatment of the anterior portions of the eye with instruments such as, by way of illustration, laser scanning ophthalmoscopes, which are actually only designed for the examination of the fundus oculi:

In order to be able examine the cornea (epithelium, endothelium), the focus plane must be moved from the retina to the cornea. This can occur by means of additionally providing in the beam path a focus lens, which is preferably attached onto the cover plate.

In the representation of the fundus oculi, by way of illustration with a scanning laser ophthalmoscope, the laser beam is focussed by the lens of the eye onto the fundus oculi, i.e. the retina. Thus an additional focussing optic is required for the representation of the anterior portions of the eye.

In the further improvement, in which the main plane facing the eye of the additional lens is at a distance from the lens of the eye, this distance is the same as the focal length of the additional lens, the size of the scanned surface and thus the enlargement is determined by the focal length of the additional lens. The scan angle remains constant in this arrangement, the focus diameter of the scanning laser beam diminishes in the same measure as the scanned distance on the cornea.

In the arrangement of the present invention, however, the scale factor does not remain constant when focussing on the different circular segments of the curved cornea.

For this reason it is particularly preferable to provide the main plane, which is arranged on the side of the instrument of examination if the additional lens is also at a distance from the focus plane of the instrument of examination and this distance is the same as the focal length of the additional lens so that the additional lens forms a telecentric system. In the event that again the eye examination instrument is a scanning laser ophthalmoscope, the scan pupil lies in the distance of the focal length before the additional lens so that the scanning beam undergoes a parallel shift after the additional lens. Due to the pre-focussing in the scanning laser ophthalmoscope, only the sharp-focus plane is changed but not the imaging scale.

If the instrument for the examination of the eye permits switching the image field, then switching between a general view representation and a detail view becomes possible without changing the contact eyeglass, respectively the additional lens.

Furthermore, one (or several) deflection mirrors can be designed as concave focussing mirrors. This permits, in particular, examination of the chamber angle.

In any case, this design has the advantage that in the case of cornea microscopy with great enlargement and corresponding small focal lengths (in the range of 20 dpt and larger) the extremely critical distance between the focussing lens, respectively the focussing mirrors, and the cornea is held constant without difficulty due to the contact eyeglass employed in accordance with the present invention, the lens of which placed on the eye has practically no spherical refractive power. On the other hand, the distance focussing optic/scan pupil of the scanning laser ophthalmoscope does not effect the sharp focus of the image, but rather the imaging scale so that this distance is not so "critical".

A BRIEF DESCRIPTION OF THE DRAWING

The present invention is made more apparent by way of example in the following section using preferred embodiments without the intention of limiting the scope and spirit of the present invention with reference to the accompanying drawing, to which express reference is made with regard to the disclosure of all the invented details not described in more detail herein.

DESCRIPTION OF THE PREFERRED EMBODIMENTS

Figure 1A:
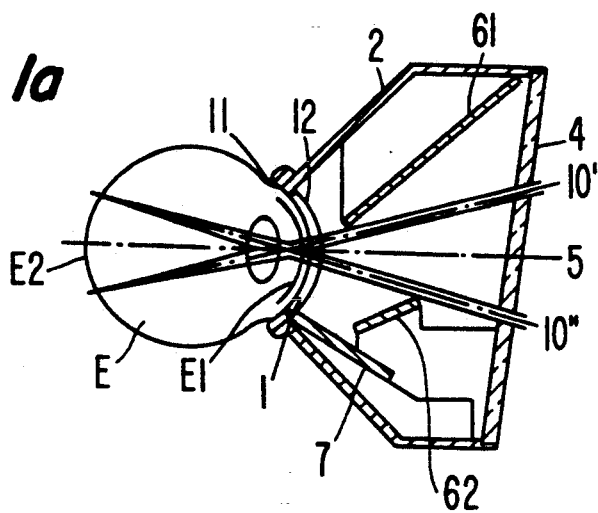
FIG. 1a shows a longitudinal section through an invented contact eyeglass.

Any instruments of examination already permitting the examination of the fundus oculi without an additional contact eyeglass may be utilized as the eye examination device in connection with the contact eyeglass described in the following section. Examination devices of this type are, by way of illustration, conventional fundus cameras, ophthalmoscopes or so-called scanning laser ophthalmoscopes as they are known, by way of illustration, from the EP-A-0 145 563, the Japanese Patent Publications 61-5730 and 50-138822, the German Patent 32 45 939 or the WO 88/ 03396. For this reason, the design of the instrument of examination will not be discussed in more detail in the following section: in some of the figures, however, the beam path of the examination device is depicted "according to the final optical surface" of the device.

FIG. 1 shows a longitudinal section through an invented contact eyeglass having a lens 1, the eye-facing surface 11 of which is curved in such a manner that the glass can be placed on the cornea E1 of an eye E to be examined. The eye-facing surface may be a spherical or even an aspherical surface, the asphericitiy of which, in particular, is selected in such a manner that the eye-facing surface 11 follows the course of the cornea.

The second surface 12 of lens 1 is selected in such a manner that lens 1 has a spherical power of partically 0 dpt in the region of the optical axis, i.e. lens 1 has no optical power for penetrating beams. If need be, this lens, however, may have aspherical power to compensate for the astigmatism of the eye.

In order to compensate for monochromatic aberrations of the eye, it is however preferable if surface 12 is an aspherical surface, the asphericity of which is selected in such a manner that it compensates for the lower refractive power of the human eye toward the periphery. If the surface sections of the usually rotational-symmetrical aspherical surfaces are described with the "aspheric equation" customary in optics so that the height of the meniscus z of the aspherical front surface, i.e. the distance in the direction of the optical axis of a surface point from the apex of the surface, is given by the following equation:

$$z = Cr^2/(1+(1-(K+1)c^2r^2)^{-\frac{1}{2}}) + C_4 \cdot r^4 + C_6 \cdot r^6 + \ldots$$

with following being:

r : the distance of the surface point from the optical axis,

C : the curvature of the surface in the apex:

$$C = 1/R = D_1/(n-1),$$

R : the radius of curvature of the surface,
K : the conic section coefficient,
$C_i$ : aspheric coefficients (i=4,6, ... )
$D_1$ : the surface refractive power in the apex,
n : the refractive index of the lens material.

The illustrated preferred embodiment may, by way of illustration, have the following values:
the radius of the eye-facing surface 11: 8.31 mm
the radius of the aspherical surface 12 in the apex:

R = 8.6 mm

K = −0.7707

$$C_4 = 2 \cdot 10^{-6}$$

$$C_6 = 1.4 \cdot 10^{-6}$$

The thickness of the lens on the optical axis is 0.5 mm and the refractive index of the glass material 1.5.

Lens 1 is held in a lens mounting 2, which is designed ergonomically easy for the examining person to handle and is terminated at its front end, i.e. the end opposite the eye E and facing the not depicted examining person, by a (transparent) dust protection cover plate, respectively a cover plate 4. Cover plate 4 is not arranged perpendicular to the optical axis 5 of the eye E to be examined and lens 1. This arrangement minimizes reflexes.

Furthermore, mirrors 61 and 62 as well as 7, which in the illustrated preferred embodiment are simple plane mirrors, are arranged in lens mounting 2. In the depicted longitudinal section, mirror 7 is drawn turned 90° compared to its actual arrangement.

In the following section, the mode of function of the contact eyeglass illustrated in FIG. 1 is to be made more apparent with reference to the part figures a to c. Without any intention of limiting the spirit and scope of the present invention, the point of departure is that the contact eyeglass is utilized with a scanning laser ophthalmoscope (SLO) with an image angle of 30°, that is in a device in which a laser illumination beam 10 performs a scanning movement on the fundus oculi, with the scanning elements being conjugated to the pupil of the eye.

In the case of the "central position" of the scanning laser ophthalmoscope illustrated in partial FIG. 1a, the two "peripheral beams 10' and 10" occurring in one scan plane" of the illumination light penetrate between the mirror arrangement 61, 62 and 7. As lens 1 has no optical power, laser beam 10 is focussed onto the fundus oculi E2 in the same manner as without the contact eyeglass placed on the eye E.

Accordingly, a treatment laser beam is also focussed onto a point to be coagulated of the fundus oculi.

If the scanning laser opthalmoscope is swung in the drawing plane, beams 10 impinge upon mirror 61, are deflected by it to mirror 62 and imaged by the latter through lens 1 onto a region of the fundus oculi E2 adjacent to the central region. The same is true for the beam of a treatment laser.

Figure 1B:
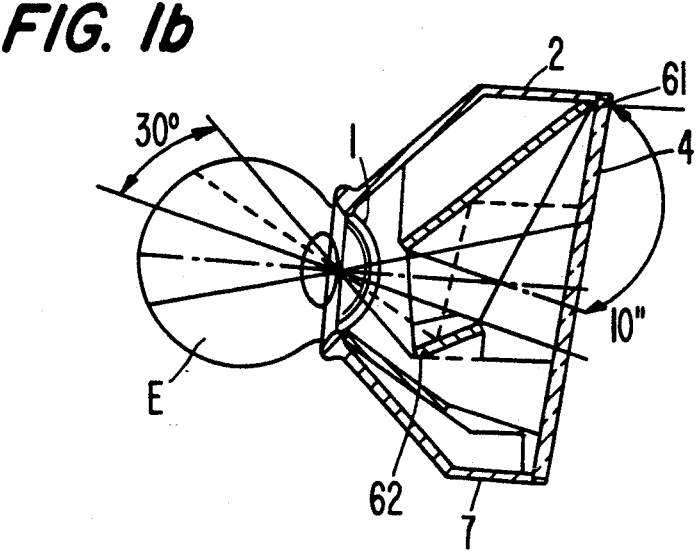
FIG. 1b shows the beam path during examination via the first set of mirrors.
Figure 1C:
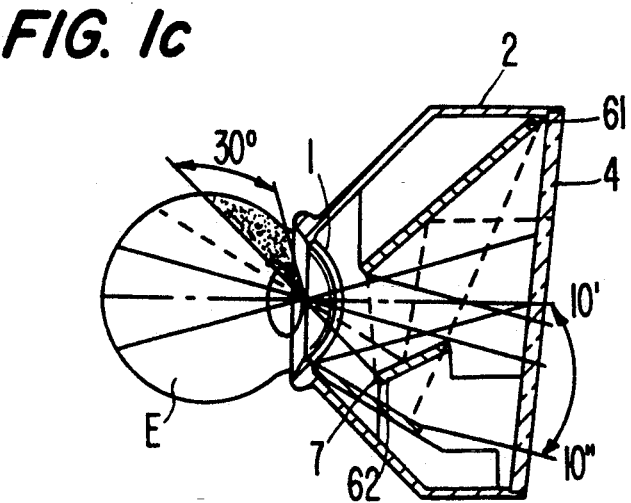
FIG. 1c shows the beam path during examination via the second set of mirrors.

In the event, the scanning laser ophthalmoscope is swung once more, the laser beam impinges upon mirror 7 and is deflected by it through lens 1 onto a very peripheral region of the fundus oculi, i.e. onto a lateral region (FIG. 1c).

In FIGS. 1b and 1c, the examination, respectively the treatment, of the fundus oculi is depicted, by way of example, in "horizontal peripheral regions". Naturally, the "vertical" examination range of the instrument for the examination of the fundus oculi can also be extended if in addition the contact eyeglass is turned about the "axis of the eye", i.e. the optical axis of the eye when the examination device is swung about a vertical axis.

Figure 2:
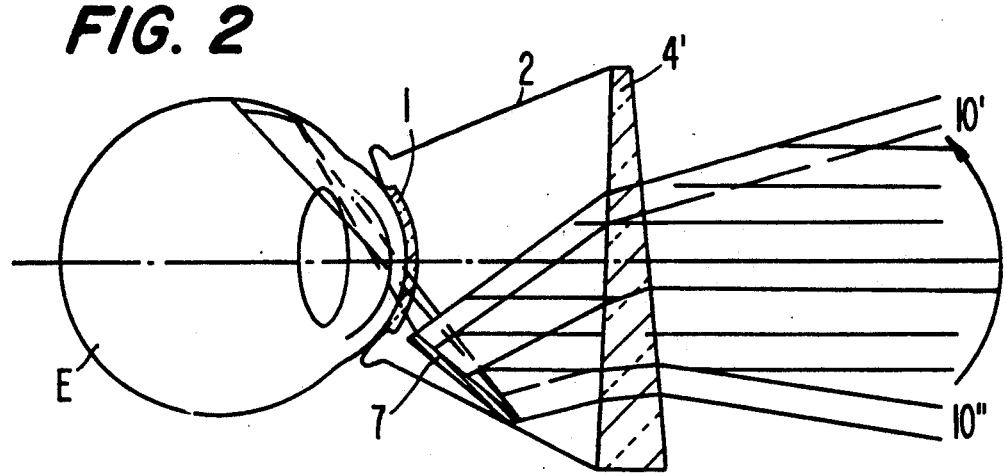
FIG. 2 shows a variation of the contact eyeglass illustrated in FIG. 1.
Figure 3:
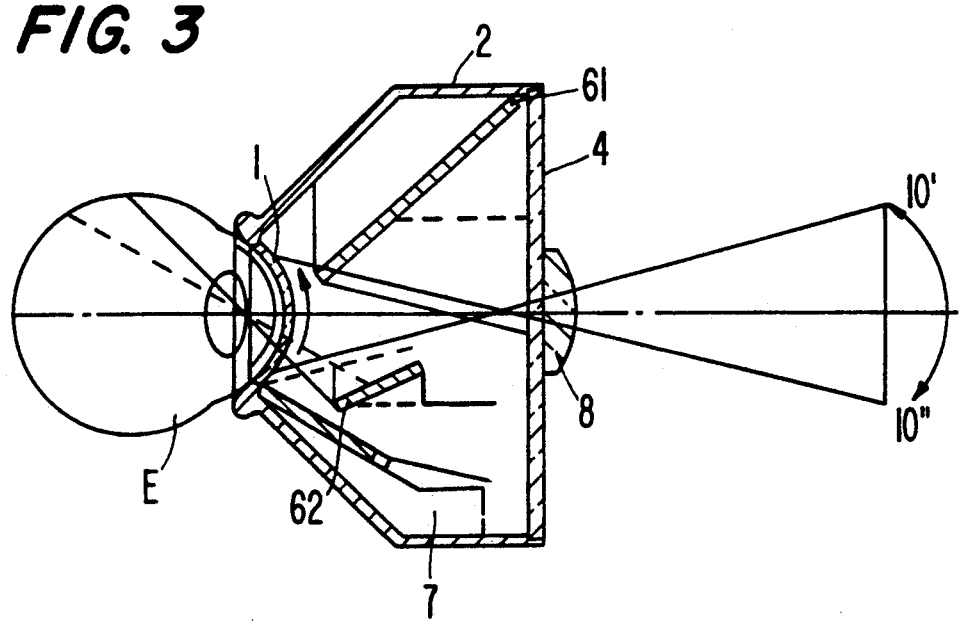
FIG. 3 shows another variation of the contact eyeglass illustrated in FIG. 1.
Figure 4:
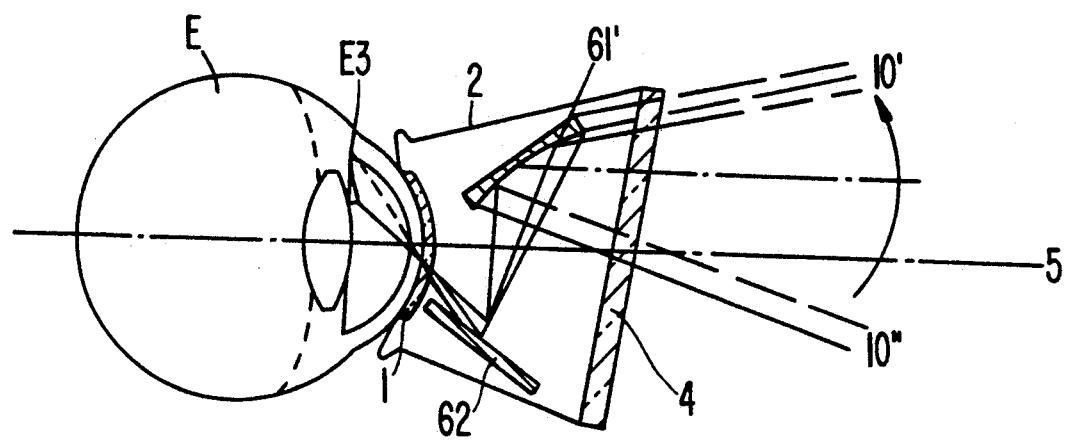
FIG. 4 shows a third variation of the contact eyeglass illustrated in FIG. 1.

FIGS. 2 to 4 show variations of the contact eyeglass illustrated in FIG. 1. The same designations stand for the same elements as in FIG. 1, thus obviating another description:

FIG. 2 shows a variation in which an extreme fundus periphery examination becomes possible due to a conic design of the cover plate 4', which thereby acts like a deflection prism.

The contact eyeglass provided in accordance with the present invention does not only extend the (horizontal and vertical) image angle of available eye examination instruments for the fundus oculi, but in addition permits the examination and/or treatment of the anterior portions of the eye with such instruments:

In order to be able to examine, e.g. the cornea (epithelium, endothelium) centrally, the focus plane has to be shifted from the retina to the cornea. This can be done according to FIG. 3 by additionally providing centrally in the beam path a focussing lens 8, which preferably is attached onto cover plate 4, respectively provided by exchanging the cover plate.

It is particularly preferable if the additional lens 8 forms a telecentric system. In the event once again that the eye examination instrument is a scanning laser ophthalmoscope, the scan pupil lies in the distance of the focal length before the additional lens so that the scanning beam undergoes a parallel shift after the additional lens. Thus pre-focussing in the scanning laser ophthalmoscope only changes the sharp-focus plane and not, however, the imaging scale.

Furthermore, according to FIG. 4, for the examination of the chamber angle, by way of illustration, the deflection mirror 61' may be designed as a concave focussing mirror typically having approx. 20 dpt in order to compensate for the focussing power of the not penetrated eye lens E3. Compared to a lens arrangement according to FIG. 3, this design has the advantage of freedom from reflexes and permits, in particular, an examination of the chamber angle without the central examination of the fundus oculi being influenced.

In the preceding section the present invention has been described using preferred embodiments without the intention of limiting the scope and spirit of the present invention, within which, of course, the most varied modifications are possible:

Thus, more than two sets of mirrors may be provided. Furthermore, the individual elements may be antireflection coated or provided with a special laser coating. Moreover, a signal giving the position of the contact eyeglass relative to the examination beam path may be entered into the image-recording system. The mirrors may also be designed moveably. Furthermore, the cover plate may be designed in such a manner that it is exchangeable and/or can be mounted with additional elements—such as additional focussing lenses, wedge prisms, etc. Naturally, special markings, etc. may also be provided. Finally the eyefacing surface 11 of lens 1 may also be designed aspherically in adaption to the geometry of the cornea.

What is claimed is:

1. An instrument for the examination and/or treatment of the eye having an examination device designed for the examination of the fundus oculi and having a contact eyeglass, which is provided with a lens which can be placed on the eye, the eye-facing surface of said lens being adapted to the curvature of the cornea, wherein said lens which is placed on the eye has no spherical power at least in the region of the optical axis.

2. An instrument according to claim 1, wherein at least a front surface of said lens is designed aspherically for the correction of monochromatic aberrations of the eye.

3. An instrument according to claim 2, wherein in an approximation of surface sections of said front aspherical surface of said lens by an ellipse said aspherical surface has an eccentricity which is larger than 0.7.

4. An instrument according to one of the claims 1 to 3, wherein at least one mirror is provided which permits the examination and/or treatment of peripheral portions of the eye.

5. An instrument according to claim 4, wherein said mirror is arranged outside an examination and/or treatment beam path for central regions of the eye.

6. An instrument according to claim 4, wherein said mirror is moveable.

7. An instrument according to one of the claim 4, wherein two sets of mirrors are provided, which permit the examination and/or treatment of different peripheral regions.

8. An instrument according to claim 7, wherein a central examination and treatment region and at least one other region, which can be examined via said mirrors, adjoin without overlapping.

9. An instrument according to claim 4, wherein at least one part of said mirror has an optical power.

10. An instrument according to claim 9, wherein said optical power of said mirror at least partially compensates for aberrations in the peripheral portions of the eye.

11. An instrument according to claim 4, wherein said lens which can be placed on the eye and said mirror are held in a contact eyeglass mounting which is terminated on the side facing away from the eye by a transparent cover plate (4).

12. An instrument according to claim 11, wherein said cover plate is designed wedge-shaped to alter the beaming-in angle.

13. An instrument according to claim 11, wherein said cover plate is arranged oblique to the optical axis of said lens which can be placed on the eye.

14. An instrument according to claim 11, wherein said cover plate is exchangeable.

15. An instrument according to claim 4, wherein for examination and/or treatment of the anterior portions of the eye an additional lens can be provided in a beam path.

16. An instrument according to claim 15, wherein the eye-facing main plane of said additional lens is at a distance from the lens of the eye, with said distance equalling the focal length of said additional lens.

17. An instrument according to claim 16, wherein the main plane arranged on the side of said examination device of said additional lens is at a distance from the focus plane of said examination device, with said distance equalling the focal length of said additional lens.

18. An instrument according to claim 15, wherein said additional lens is mounted on said cover plate (4).

19. An instrument according to claim 15, wherein markings are provided on said cover plate and/or on said mirror.

20. An instrument according to claim 4, wherein said lens is held in a contact eyeglass mounting and said at least one mirror is separate from members forming said eyeglass mounting.

* * * * *